United States Patent [19]

Sekine et al.

[11] Patent Number: 4,985,242

[45] Date of Patent: Jan. 15, 1991

[54] INTRANASALLY APPLICABLE POWDERY PHARMACEUTICAL COMPOSITION

[75] Inventors: Kunio Sekine; Daisuke Araki; Yoshiki Suzuki, all of Hino, Japan

[73] Assignee: Teijin Limited, Osaka, Japan

[21] Appl. No.: 132,447

[22] Filed: Dec. 14, 1987

Related U.S. Application Data

[63] Continuation of Ser. No. 832,932, Feb. 25, 1986, abandoned.

[30] Foreign Application Priority Data

Feb. 25, 1985 [JP] Japan ................................ 60-34581

[51] Int. Cl.$^5$ .................... A61K 37/66; A61K 39/00; A61K 37/00; A61K 37/26
[52] U.S. Cl. .................................. 424/85.4; 424/85.8; 514/2; 514/3; 514/11; 514/12
[58] Field of Search ....................... 514/3, 4, 2, 12, 11, 514/800, 808, 15, 807; 424/85.8, 85.4

[56] References Cited

U.S. PATENT DOCUMENTS 4,613,500  9/1986  Suzuki et al. ..................... 424/46

FOREIGN PATENT DOCUMENTS 58-189118  11/1983  Japan .
59-89619   5/1984   Japan .
59-130820  7/1984   Japan .
59-163313  9/1984   Japan .

OTHER PUBLICATIONS

S. Hirai et al, Diabetes vol. 27, p. 296, (1978).

*Primary Examiner*—Frederick E. Waddell
*Attorney, Agent, or Firm*—Sughrue, Mion, Zinn, Macpeak & Seas

[57] ABSTRACT

An intranasally applicable powdery pharmaceutical composition comprising a polypeptide having a physiological activity, a quaternary ammonium compound, and a lower alkyl ether of cellulose. This powdery pharmaceutical composition has an excellent preservability and chemical stability of the polypeptides and, when the powdery composition is administered to the nasal cavity in the form of a spray, the polypeptides are effectively absorbed through the nasal mucosa.

12 Claims, No Drawings

INTRANASALLY APPLICABLE POWDERY PHARMACEUTICAL COMPOSITION

This is a continuation of Ser. No. 832,932, filed Feb. 25, 1986, now abandoned.

BACKGROUND OF THE INVENTION

1. Field of the Invention

The present invention relates to a novel intranasally applicable powdery pharmaceutical composition comprising a polypeptide having a physiological activity, a quaternary ammonium compound, and a lower alkyl ether of cellulose. More specifically, it relates to an intranasally applicable powdery pharmaceutical composition comprising a physiologically active polypeptide such as calcitonin and insulin, a quaternary ammonium compound such as benzalkonium chloride, and a lower alkyl ether of cellulose. This powdery composition has an excellent chemical stability and preservability of the polypeptides and, when this powdery composition is administered to the nasal cavity in the form of a spray, the polypeptides are effectively absorbed through the or nasal mucosa.

2. Description of the Related Art

Since peptide hormones such as insulin and calcitonin have a large molecular weight and are easily decomposed by proteinases such as pepsin, trypsin, and chymotrypsin, they are not easily absorbed by oral administration and, therefore, the intended pharmacological effects cannot be effectively exhibited. Accordingly, such peptide hormones are generally administered by injection. However, since the injectable administration is generally painful, various other administration methods have been proposed For example, J. Pharm. Pharmacol., 33, 334 (1981) discloses rectal absorption of insulin and heparin in a suppository in which salicylic acid derivatives such as sodium salicylate, sodium 3-methoxysalicylate, and 5-methoxysalicylate are used as an absorption aid. Furthermore, other methods such as intratracheal administration methods (see Diabetes 20, 552, 1971) and eye instillation methods (see Tonyobyo Gakkai Shoshu, Japan, 237, 1974) are being studied. However, since these methods are disadvantageous in that high dosage amounts are required when compared with the injection, and that the absorption amounts are likely to vary, these methods are not practically acceptable.

On the other hand, as disclosed in, for example, Diabetes, 27, 296, 1978, as well as Japanese Unexamined Patent Publication (Kokai) Nos. 59-89619 and 59-130820, intranasally applicable liquid pharmaceutical preparations of insulin or calcitonin containing, as an absorption aid, certain surfactants, are proposed for administration to the nasal cavity. Furthermore, Japanese Unexamined Patent Publication (Kokai) No. 58-189118 discloses intranasally applicable liquid pharmaceutical preparations of insulin in which cyclodextrin is used.

However, for the intranasally applicable liquid pharmaceutical preparation of, for example, insulin or calcitonin, it is necessary to ensure that contamination of the liquid preparations caused by the invasion of, for example, microorganisms, is prevented. It is proposed in Japanese Unexamined Patent Publication (Kokai) No. 59-89619 that benzalkonium chloride be included in the intranasally applicable liquid pharmaceutical preparations to prevent such contamination, and to enhance the preservability of medicines such as calcitonin.

Intranasally applicable powdery pharmaceutical preparations containing calcitonin, insulin, or the like, and lower alkyl ethers of cellulose are also known, as disclosed in Japanese Unexamined Patent Publication (Kokai) No. 59-163313. However, it is still necessary to improve the preservability of the medicines such as calcitonin and insulin and also to enhance the chemical stability of the medicines such as calcitonin and insulin even in these powdery preparations.

SUMMARY OF THE INVENTION

Accordingly, the object of the present invention is to improve or increase the preservability and the chemical stability of medicines, such as calcitonin and insulin, of intranasally applicable powdery pharmaceutical compositions comprising medicines such as calcitonin and insulin and lower alkyl ethers of cellulose Other objects and advantages of the present invention will be apparent from the following description.

According to the present invention, there is provided an intranasally applicable powdery pharmaceutical composition comprising a polypeptide having a physicological activity, a quaternary ammonium compound, and a lower alkyl ether of cellulose.

In accordance with the preferred embodiment of the present invention, the above-mentioned intranasally applicable powdery pharmaceutical composition is prepared by mixing (i) a lyophilized mixture of the polypeptide having a physiological activity, a portion or total amount of the quaternary ammonium compound, and a portion of the lower alkyl ether of cellulose, (ii) the remainder of the lower alkyl ether of cellulose, and, optionally (iii) the remainder of the quaternary ammonium.

DESCRIPTION OF THE PREFERRED EMBODIMENTS

According to the present invention, the desired powdery pharmaceutical composition, i.e., a composition having an extremely excellent preservability and chemical stability of polypeptides such as calcitonin and insulin can be obtained by incorporating the above-mentioned quaternary ammonium compound, together with the lower alkyl ether of cellulose into the powdery composition containing the physiologically active polypeptide (e.g., calcitonin or insulin). In addition, when a mixture of the physiologically active polypeptide (e.g., calcitonin or insulin), a portion of the lower alkyl ester of cellulose, and a portion or total amount of the quarternany ammonium compound is used in the form of a lyophilized product for the preparation, the desired powdery pharmaceutical composition having the polypeptide and the quarternary ammonium compound uniformly dispersed therein and having an excellent preservability and chemical stability can be obtained.

The polypeptides usable in the present invention are those having physiological activities. The preferable polypeptides usable in the present invention are those having a molecular weight of 300 to 300,000, especially 1,000 to 150,000, because such polypeptides are easily absorbed through the nasal mucosa.

Typical examples of the polypeptides having physiological activities are peptide hormones such as insulin, angiotensin, vasopressin, desmopressin, felypressin, protirelin, luteinizing hormone-releasing hormone, corticotropin, prolactin, somatotropin, thyrotropin, luteinizing hormone, calcitonin, kallikrein, parathyrin, glucagon, oxytocin, gastrin, secretin, gonadotropic hormone, growth hormone, erythropoietin, angiotensin, urogastrone, renin, lypomodulin, calmodulin, human atrial natriuretic polypeptide (i.e., hANP), and the chemically modified compounds thereof or the components thereof; physiologically active proteins such as interferons, interleukins, transferrin, histaglobulin, macrocortin, and blood coagulation factor VIII; zymoproteins such as lysozyme and urokinase; and vaccines such as pertussis vaccine, diphtheria vaccine, tetanus vaccine, influenza virus vaccine, lymphocytosis promoting factor, and filamentous hemagglutinin. Of those polypeptides, peptide hormones are suitable for use in the present invention. Preferable examples of the polypeptides are calcitonin, insulin, luteinizing hormone-releasing hormones, desmopressin, vasopressin, and oxytocin, especially preferably calcitonin and insulin.

The amount of the polypeptides in the intranasally applicable powdery pharmaceutical compositions according to the present invention may be widely varied depending upon the kinds of polypeptides to be used. For example, calcitonin is generally incorporated into the powdery composition in an amount of 0.2 to 16 MRC unit/mg, and insulin is generally incorporated into the powdery composition in an amount of 0.016 to 6.4 unit/mg.

The quaternary ammonium compounds usable in the present invention can be of either any known quaternary ammonium compounds or newly synthesized compounds. Typical examples of the quaternary ammonium compounds are benzalkonium chloride, benzethonium chloride, cetyl trimethyl ammonium bromide, dodecyl dimethyl ammonium bromide, and methylrosaniline chloride. Of these quaternary ammonium compounds, benzalkonium chloride, and benzethonium chloride are especially preferably used. These quaternary ammonium compounds may be used alone or in any mixture thereof.

Although there is no critical amount of the quaternary ammonium compounds to be included in the present powdery composition, the quaternary ammonium compounds are generally included in the present composition in an amount of about 0.001% to 12% by weight, preferably 0.025% to 1% by weight, more preferably 0.05% to 0.5% by weight, based on the total weight of the composition.

The lower alkyl ethers of cellulose usable in the present invention may be those obtained by at least partially substituting the same or different lower alkyl ether groups for a plurality of hydroxyl groups of cellulose. The lower alkyl groups in the lower alkyl ether groups may be partially substituted with substituents. Examples of such preferable substituents are hydroxyl groups and carboxyl groups.

The term "lower alkyl" used herein means an alkyl group having 5 or less carbon atoms, preferably 3 or less carbon atoms. Examples of the optionally substituted lower alkyl groups are methyl, ethyl, n-propyl, iso-propyl, β-hydroxyethyl, and β-hydroxypropyl.

Typical examples of the lower alkyl ethers of cellulose usable in the present invention are methyl cellulose, ethyl cellulose, propyl cellulose, hydroxyethyl cellulose, hydroxypropyl cellulose, carboxymethyl cellulose, carboxyethyl cellulose, carboxymethyl hydroxyethyl cellulose, and hydroxypropylmethyl cellulose. Of these lower alkyl ethers of cellulose, the use of hydroxypropyl cellulose, methyl cellulose, hydroxyethyl cellulose, or hydroxypropylmethyl cellulose is preferable in the present invention. The use of hydroxypropyl cellulose is most preferable in the present invention. These lower alkyl ethers of cellulose may be used alone or in any mixture thereof in the present invention. There is no limitation in the molecular weight and the ether substitution degree of the above-mentioned lower alkyl ethers of cellulose. For example, any commercially available lower alkyl ethers of cellulose can be used in the present invention. However, the lower alkyl ethers of cellulose having a viscosity, in a 2 w/v % aqueous solution thereof, of 3 to 100,000 cp, more preferably 3 to 10,000 cp, especially preferably, 5 to 6000 cp, are preferably used in the present invention.

The intranasally applicable powdery compositions according to the present invention can be prepared in any conventional manner. For example, the present powdery composition can be prepared by mechanically mixing the above-mentioned three essential constituents, i.e., the polypeptides having a physiological activity, the quaternary ammonium compounds, and the lower alkyl ethers of cellulose, and optional ingredients, if any. That is, the present powdery composition may be prepared by adding the polypeptides and the quaternary ammonium compounds to the lower alkyl ethers of cellulose, followed by mixing However, preferably, a mixture of the polypeptides, a portion of the lower alkyl ethers of cellulose, and a portion of or a total amount of the quaternary ammonium compounds are first lyophilized and the resultant lyophilized mixture is then mixed with the remainder of the lower alkyl ethers of cellulose and, optionally, the quaternary ammonium compounds.

When the polypeptides and the quaternary ammonium compounds are added to the lower alkyl ethers of cellulose, the resultant mixture is mechanically mixed by any conventional method, followed by sifting. Thus, the desired intranasally applicable powdery composition according to the present invention can be prepared. In this case, the lyophilized polypeptides may be used. Furthermore, when the mixing is carried out in any conventional manner, the so-called co-pulverization method can be used so that the polypeptides and the quaternary ammonium compounds may be dispersed in the molecular level dispersion degree in the lower alkyl ethers of cellulose.

On the other hand, when the lyophilized mixture of the polypeptides, the quaternary ammonium compounds, and the lower alkyl ethers of cellulose is mixed with the lower alkyl ethers of cellulose and, optionally, the quaternary ammonium compounds, the polypeptides and the quaternary ammonium compounds are suffciently uniformly dispersed in the lower alkyl ethers of cellulose and, therefore, the resultant powdery compoisition has a more preferably improved preservability and chemical stability of the polypeptides.

The above-mentioned lyophilized mixture can be obtained by uniformly dissolving the polypeptides, the quaternary ammonium compounds, and the lower alkyl ethers of cellulose in water by appropriately adjusting the pH of the aqueous solution, if necessary. The resultant aqueous solution can be lyophilized in any conventional manner. The lyophilized mixture is then mechanically mixed with the lower alkyl ethers of cellulose and, optionally, the quaternally ammonium compounds, followed by sifting the resultant mixture as mentioned above.

When the lower alkyl ethers of cellulose and the quaternary ammonium compounds are lyophilized, the lower alkyl ethers of cellulose are generally lyophilized in an amount of about 0.01% to 10% by weight, preferably 0.1% to 5% by weight of the total amount of the lower alkyl ethers of cellulose included in the powdery compoisition from the viewpoints of improving the stability of the polypeptides. On the other hand, the quaternally ammonium compounds can be lyophilized generally in an amount of about 0.01% to 100% by weight (i.e., entirely), preferably 0.1% to 10% by weight of the total amount thereof included in the present powdery composition, provided that the total amount thereof is within the above-mentioned range.

Although there is no specific limitation in the particle size of the present powdery pharmaceutical composition, the particle size of the present powdery composition is preferably such that at least about 90% by weight of the powder particles has an effective particle diameter of about 10 to 250 μm. When the powder particles having a particle size of less than about 10 μm are present in the powdery composition in an amount of more than 10% by weight, a relatively large amount of the powdery composition unpreferably reaches the lungs or is unpreferably scattered out of the nasal cavity when the powdery composition is administered to the nasal cavity by for example, spraying. In addition, it is difficult to maintain the high or desired polypeptide concentration at the portion of the nasal mucosa to which the applied powdery composition adheres. Contrary to this, when the powder particles having a particle size of more than about 250 μm are present in the powdery composition in an amount of more than 10% by weight, the powder particles adhered to the nasal mucosa when applied by spraying are likely to be mechanically released from the mucosa surface and, therefore, the local retentionability of the powder particles is decreased. For these reasons, the present powdery pharmaceutical compositions preferably have a particle size distribution such that at least about 90% by weight of the powder particles has an effective particle size of about 10 to 250 μm.

The intranasally applicable powdery composition according to the present invention may optionally contain various conventional additives for improving the physical properties, visual appearance, or odor of the composition. Examples of such additives are lubricants such as talc, stearic acid and the salts thereof; waxes; binders such as starch, dextrin, cyclodextrin, tragancanth gum, gelatin, polyvinylpyrrolidone, and polyvinyl alcohol; diluents such as starch, crystalline cellulose, dextrin, cyclodextrin, lactose, mannitol, sorbitol, and anhydrous calcium phosphate; coloring agents such as copper chlorophyll, β-carotene, Red #2 (i.e., trisodium salt of 1-(4-sulfo-l-naphthylazo)-2-naphthol-3,6-disulfonic acid), Blue #2 (i.e., disodium salt of 5,5'-indigotindisulfonic acid); odor improves such as menthol and citrus perfumes; anti-oxidants such as ascorbic acid, erythrobic acid and the salts and esters thereof; bulk fillers such as human serum albumin, mannitil, and sorbitol; isotonic agents such as sodium chloride and glucose; and surfactants which are physiologically non-toxic. Typical examples of such surfactants are sorbitan fatty acid esters, polyoxyethylene sorbitan fatty acid esters, glycerol fatty acid esters, sucrose fatty acid esters, glicolic acid, taurucholic acid and salts thereof, polyoxyalkylene higher alcohol ethers (e.g., polyoxyethylene and polyoxypropylene lauryl, cetyl, and cholestryl ethers). Suitable absorption aids also may be used in the present invention.

The intranasally applicable powdery pharmaceutical composition can be directly formulated into a powder preparation in a unit dosage form. Such a powder preparation may be preferably included in a capsule such as a hard gelatine capsule as a preferred dosage form for the nasal application. The unit dosage of the powder preparation of the present invention is preferably about 1 to 100 mg, more preferably 5 to 50 mg, although this amount may be widely varied depending upon the kind of physiologically active polypeptides.

The present powder preparations can be advantageously applied to the nasal cavity. For example, a capsule filled with the present powder preparation is set in a spraying device equipped with a needle. The capsule is pierced with the needle to provide minute holes on the bottom sides. The powder preparation is then sprayed or jetted out from the capsule by sending air into the capsule by means of, for example, a rubber ball.

As explained above, according to the present invention, intranasally applicable powdery pharmaceutical compositions having an improved preservability and chemical stability of the physiologically active polypeptides included therein are advantageously provided.

EXAMPLE

The present invention will now be described in detail with reference to, but is by no means limited to, the following examples.

EXAMPLE 1

(a) A 10 mg amount of hydroxypropyl cellulose and 0.2 mg of salmon calcitonin (4000 MRC unit/mg) were dissolved in 5 ml of distilled water. To the resultant solution, 10 μl of a 0.02 w/v % benzalkonium chloride solution was added while stirring. The mixture was lyophilized. Thus, the uniform powdery composition (I) of salmoncalcitonin and hydroxypropyl cellulose containing 0.02 w/w % of benzalkonium chloride and having a calcitonin activity of 78.4 MRC unit/mg was obtained.

Then, 10 mg of the powdery composition (I) and 800 mg of hydroxypropyl cellulose were placed in a mortar and 0.16 mg of benzalkonium chloride was added thereto. The mixture was thoroughly mixed in the mortar. Thus, a uniform powdery composition (II) is obtained having a particle size distribution such that 90 w/w % or more of the powder particles had a particle size of 25 to 149 μm. The powdery composition (II) thus obtained containing 0.02 w/w % of benzalkonium chloride has a calcitonin activity of about 0.97 MRC unit/mg.

The powdery composition (II) obtained above was filled in hard gelatin capsules in an amount of 10 to 50 mg per each capsule to prepare intranasally applicable pharmaceutical preparations for humans.

(b) A 10 mg amount of hydroxypropyl cellulose and 0.2 mg of salmon calcitonin (4000 MRC unit/mg) were dissolved in 5 ml of distilled water and 10 μl of a 0.05 w/v % benzethonium chloride solution. The resultant mixture was lyophilized to obtain a uniform powdery composition (I) of salmon calcitonin and hydroxypropyl cellulose containing 0.05 w/w % of benzethonium chloride and having a calcitonin activity of about 78 MRC unit/mg.

Then, 10 mg of the powdery composition (I) and 800 mg of hydroxypropyl cellulose were placed in a mortar and 0.4 mg of benzethonium chloride was added thereto. The mixture was thoroughly mixed in the mortar. Thus, a uniform powdery composition (II) was obtained having a particle size distribution such that 90 w/w % or more of the powder particles had a particle size of 25 to 149 μm. The powdery composition (II) thus obtained containing 0.05 w/w % of benzethonium chloride has a calcitonin activity of about 0.96 MRC unit/mg.

The powdery composition (II) obtained above was filled in hard gelatin capsules in an amount of 10 to 50 mg per each capsule to prepare intranasally applicable pharmaceutical preparations for humans.

EXAMPLE 2

Evaluation of Pharmacological Stability in Intranasally Applicable Powdery Composition The intranasally applicable salmon calcitonin powdery preparations prepared in Example 1(a) and (b) were allowed to stand at a temperature of 40° C. for 2 months. The stability of salmon calcitonin in the powdery preparations was determined as follows:

The samples after 2 months storage and the fresh or standard samples (i.e., the samples taken immediately after the preparation) were dissolved in injection liquid in such a manner that the content of the salmon calcitonin become 0.083 μg/ml in terms of the standard sample. Thus, the injection liquid samples for a stability evaluation of the salmon calcitonin were prepared.

The above-mentioned injection liquid samples were intramuscularly injected into a thigh portion of SD type male rats having a body weight of 160 to 180 g (6 weeks old, five rats per one group) in such a manner that the administration amount of the salmon calcitonin was 0.083 μg/ml/kg. The whole blood was sampled 1 hour after administration and the serum was recovered therefrom after the blood sample was allowed to stand at room temperature for 0.5 to 1 hour. The calcium concentration in the serum was determined by means of a calcium content determining kit (manufactured by IATRON) from the decreasing degree of the calcium concentration in the serum, the percentage of the salmon calcitonin remaining in the injection sample was determined. That is, a calibration curve between the calcium concentration in the serum and the administration amount of the salmon calcitonin was previously obtained by using the standard sample. The residual percentages of the salmon calcitonin in the injection samples were determined from the calbration curve.

The results are as shown in Table 1.

As Comparative Examples, the following liquid preparations (a) and (b) were prepared.

Preparation of Comparative Liquid Preparation (a)

A 400 mg amount of hydroxypropyl cellulose was first dissolved in 100 ml of purified water. Then, in 5 ml of the resultant 0.4 w/v % hydroxypropyl cellulose solution, 0.326 mg of salmon calcitonin having a calcitonin activity of 4000 MRC unit/mg was dissolved and 1 mg f benzalkonium chloride was further dissolved therein. Thus, an intranasally applicable salmon calcitonin liquid preparation (a) containing 0.4 w/v % of hydroxypropyl cellulose and 0.02 w/v % of bezalkonium chloride was obtained. This liquid preparation (a) contained about 260 MRC unit/ml of salmon calcitonin.

Preparation of Comparative Liquid Preparation (b)

The intranasally applicable liquid preparation (b) was prepared in the same manner as in the case of the liquid preparation (a) except that the hydroxypropyl cellulose was not used. The resultant liquid preparation contained about 260 MRC unit/ml of salmon calcitonin.

The residual percentages of the salmon calcitonin in the liquid preparations (a) and (b) were determined in the same manner as mentioned above. The results are as shown in Table 1.

As clearly shown in Table 1, there was no substantial difference in the salmon calcitonin amount between the fresh or standard samples and the samples after being allowed to stand at a temperature of 40° C. for 2 months. Contrary to this, in the case of the comparative liquid preparation samples (a) and (b), the residual salmon calcitonin percentage were only about 50% and about 10%, respectively. In addition, in the case of the powdery samples (a) and (b), there was no substantial difference in the serum calcium concentrations between the fresh samples and the samples after storing at 40° C. for 2 months. Contrary to this, in the case of the comparative samples, the serum calcium concentrations were significantly increased when the samples after allowing to stand at 40° C. for 2 months were administered.

TABLE 1

Residual Percentages of Salmon Calcitonin

| Sample Preparation | Residual (%) | |
|---|---|---|
| | Fresh or Standard Sample | After 40° C. × 2 months |
| Powdery Sample (a) of Example 1 | about 100 | about 100 |
| Powdery Sample (b) of Example 1 | about 100 | about 100 |
| Comparative Liquid Sample (a) | about 100 | about 50 |
| Comparative Liquid Sample (b) | about 100 | about 10 |

EXAMPLE 3

(a) A 100 mg amount of insulin (25.5 unit/mg) and 0.195 mg of benzalkonium chloride were weighed into a mixer, and 1200 mg of hydroxypropyl cellulose was then added thereto, as a base in the powdery preparation. These three components were thoroughly mixed in the mixer to prepare a uniform powdery composition having a particle size distribution such that 90 w/w % or more of the powder particles had a particle size of 44 to 149 μm. The resultant powdery composition had an insulin activity of about 1.96 unit/mg.

(b) A 100 mg amount of lyophilized water-soluble insulin having an activity of 25.5 unit/mg, which was obtained by dissolving insulin in water, followed by lyophilizing, and 0.37 mg of benzalkonium chloride were weighed into a mixer, and 3600 mg of hydroxypropyl cellulose was then added thereto, as a base in the powdery preparation. These three components were thoroughly mixed in the mixer to prepare a uniform powdery composition having a particle size distribution such that 90 w/w % or more of the powder particles had a particle size of 44 to 149 μm. The resultant powdery composition had an insulin activity of about 0.69 unit/mg.

(c) The powdery compositions (a) and (b) containing the insulin prepared above were filled in capsules, respectively. Thus, intranasally applicable insulin preparations for humans were prepared.

EXAMPLE 4

(a) A 2000 mg amount of hydroxypropyl cellulose and 0.6 mg of salmon calcitonin (4000 MRC unit/mg) were weighed in a mixer, and 0.4 mg of benzalkonium chloride was then added thereto. These three components were thoroughly mixed in the mixer to prepare a uniform powdery composition having a particle size distribution such that 90 w/w % or more of the powder particles had a particle size of 44 to 149 μm. The resultant powdery composition contained about 1.2 MRC/mg of salmon calcitonin.

The resultant powdery composition was filled in capsules in an amount of 10 to 50 mg by using a capsule filling apparatus. Thus, intranasally applicable preparations for humans were obtained.

(b) A 2000 mg amount of hydroxypropyl cellulose and 0.7 mg of salmon calcitonin having an activity of 4000 MRC unit/mg were weighed in a mixer, and 0.3 g of benzethonium chloride was then added thereto. These three components were thoroughly mixed in the mixer to prepare a uniform powdery composition having a particle size distribution such that 90 w/w % or more of the powder particles had a particle size of 44 to 149 μm. The resultant powdery composition contained about 4 MRC/mg of salmon calcitonin.

The resultant powdery composition was filled in capsules in an amount of 10 to 50 mg by using a capsule filling apparatus. Thus, intranasally applicable preparations for humans were obtained.

EXAMPLE 5

A 980 mg amount of hydroxypropyl cellulose was weighed in a mortar and 20 mg of vasopressin (70 to 100 unit/mg) and 0.1 mg of bezalkonium chloride were added thereto. After mixing thoroughly, a uniform powdery composition was obtained. The resultant powdery composition contained about 1.4 to 2.0 unit/mg of vasopressin.

The powdery composition was filled in capsules to obtain intranasally applicable preparations for humans.

EXAMPLE 6

A 990 mg amount of hydroxypropyl cellulose was weighed in a mortar and 10 mg of luteinizing hormone-releasing hormone and 0.1 mg of benzalkonium chloride were added thereto. After mixing thoroughly, a uniform powdery composition having a particle size distribution such that 90 w/w % or more of the powder particles had a particle size of 44 to 149 μm was obtained. The resultant powdery composition contained 10 μg/mg of the luteinizing hormone-releasing hormone.

The resultant powdery composition was filled in capsules. Thus, intranasally applicable preparations for humans were obtained.

EXAMPLE 7

A 950 mg amount of hydroxypropyl cellulose was weighed in a mortar and 50 mg of interferons (100,000 unit/mg), which was previously lyophilized by adding human serum albumin, and 0.15 mg of benzalkonium chloride were added thereto. After mixing thoroughly, a uniform powdery composition having a particle size distribution such that 90 w/w % or more of the powder particles had a particle size of 44 to 149 μm was obtained. The resultant powdery composition contained 5000 unit/mg of the interferons.

The resultant powdery composition was filled in capsules. Thus, intranasally applicable preparations for humans were obtained.

EXAMPLE 8

The contamination degree due to microorganisms of the intranasally applicable powdery compositions prepared in Example 1(a) and (b) and Example 4(a) and (b) was evaluated according to a method described in "The Microbial Limit Tests of Preparations for Oral Use and Contrast Media for Roentgenography" (Yakuhatsu vol. 297, 1976).

According to the test results for the above-mentioned samples, in the case of the bacteria test, even when the water content of the powdery composition samples was 12% or more, the number of living cells was less than 30 cells/g, determined by most probable number and E. coli, Pseudomonas aeruginosa, and coccus were not determined. In addition, in the case of fungi, the number of living cells was less than 3 cells/g determined by most probable number.

Contrary to the above, the intranasally applicable powdery compositions containing no quaternary ammonium compounds satisfied the conditions necessary to be determined as stable against microorganism contamination. However, they exhibited a number of living cells of less than 80 cells/g determined by most probable number in the case of the bacterium test and a number of living cells of less than 10 cells/g determined by most probable number in the case of the fungus test, when the water content of the powdery composition sample was 12% or more.

As is clear from the results shown above, the intranasally applicable powdery compositions according to the present invention were extremely stable against unpreferable microorganism contamination.

EXAMPLE 9

(i) Preparation (a) A 300 mg amount of hydroxypropyl cellulose and 163 μg of salmon calcitonin (4000 MRC unit/mg) were weighed in an agate mortar. Then, 60 μg of benzalkonium chloride was added thereto. These three components were thoroughly mixed. Thus, a uniform powdery composition having a particle size distribution such that 90 w/w % or more of the particles had a particle size of 44 to 149 μm was obtained.

The powdery composition thus obtained contained about 0.543 μg/mg of salmon calcitonin. The powdery composition was filled in capsules in such an amount that 1.8 mg per 1 kg of rabbit (i.e., 0.978 μg of salmon calcitonin per 1 kg of rabbit) was included in each capsule. Thus, an intranasally applicable powdery preparation (a) was prepared.

(b) A 400 mg amount of hydroxypropyl cellulose was dissolved in 100 ml of purified water. In 5 ml of the resultant 0.4 w/v % hydroxypropyl cellulose solution, 163 μg of salmon calcitonin (4000 MRC unit/mg) was dissolved and, furthermore, 500 μg of benzalkonium chloride was dissolved therein. Thus, an intranasally applicable liquid preparation (b) containing 0.4 w/v % of hydroxypropyl cellulose and 0.01 w/v % of benzalkonium chloride was prepared. This liquid preparation contained about 32.6 μg/ml of salmoncalcitonin.

(ii) Evaluation Test

The powdery calcitonin preparation (a) and the liquid calcitonin preparation (b) obtained above were administered into the nasal cavity of Japanese white male rabbits, having a body weight of 2.5 to 3.5 kg, in an amount of 0.978 μg/1.8 mg/kg (i.e., about 3.9 MRC unit/kg) and 0.978 μg/30 μl/kg (i.e., about 3.9 MRC unit/kg), respectively.

The blood samples were taken from the auris vein of the rabbits before the administration and 30 minutes, 1, 2, 4, and 6 hours after the administration.

The administration to the nasal cavity was carried out under aparalytic conditions (i.e., ordinary conditions) by using, in the case of the powdery preparation, a nebulizer modified for animals, or by using, in the case of the liquid preparation, a 1 ml syringe provided with a chip for a micropipette at the tip thereof so as to be able to quantitatively administer viscous liquid.

The calcium concentrations in the serum before and after the administration were determined and the absorbability of the calcitonin through the nasal mucosa was studied. The determination of the calcium concentrations in the serum was carried out by using a calcium determination kit (manufactured by IATRON).

The results are shown in Table 2, in which the descent percentages of the calcium concentration in serum from the concentrations before administration are shown for an average of 8 or 9 rabbits.

TABLE 2

| Sample | Descent (%) of Calcium in Serum | | | | |
|---|---|---|---|---|---|
| | 30 minutes | 1 hr | 2 hr | 4 hr | 6 hr |
| Powdery Calcitonin Preparation (a) | 6.5 | 15.8 | 14.3 | 4.7 | 1.6 |
| Liquid Calcitonin Preparation (b) | 7.3 | 12.7 | 12.0 | 2.0 | 0.3 |

As clear from the results shown in Table 2, the absorbability of the powdery calcitonin preparation (a) according to the present invention is superior to that of the liquid calcitonin preparation (b).

EXAMPLE 10

Absorbability of Insulin of Intranasally Applicable Powdery Composition (i) Preparation (a) A 100 mg amount of insulin (25.5 unit/mg) and 0.195 mg of benzalkonium chloride were weighed into a mixer and 1200 mg of hydroxypropyl cellulose was then added thereto, as a base in the powdery preparation. These three components were thoroughly mixed in the mixer to prepare a uniform powdery composition having a particle size distribution such that 90 w/w % or more of the powder particles had a particle size of 44 to 149 μm. The resultant powdery composition had an insulin activity of about 1.96 unit/mg.

The powdery composition was filled in capsules to obtain an intranasally applicable insulin preparation.

(b) An intranasally applicable insulin preparation was prepared in the same manner as in (a) mentioned above, except that 1200 mg of lactose was used instead of the hydroxypropyl cellulose.

(ii) Administration of Insulin

The intranasally applicable insulin preparations (a) and (b) obtained above were administered into the nasal cavity of Japanese white male rabbits having a body weight of 3.1 to 3.7 kg in an amount of 5 unit/kg in terms of the insulin activity.

The blood samples were taken from the auris vein of the rabbits before the administration and 30 minutes, 1, 2, 4, and 6 hours after the administration. The blood sample thus taken was centrifugally separated at 2800 r.p.m. for 10 minutes in a centrifugal separator to recover the serum. The administration of the intranasally applicable insulin preparation was carried out by using a nebulizer modified for animals under ordinary conditions. The glucose concentration in the serum was determined by a method using o-toluidine (see: Clinical Chemistry, 8, 215, 1962). The change of the glucose in the serum is shown as a blood sugar descending percentage (%). The value shown in Table 3 is an average of the data for 5 rabbits.

TABLE 3

| Sample | Blood sugar descending percentage (%) | | | | |
|---|---|---|---|---|---|
| | 30 min. | 1 hr | 2 hr | 4 hr | 6 hr |
| Preparation (a) | 14 | 34 | 37 | 16 | 4 |
| Preparation (b) | 8 | 14 | 6 | 0.5 | 2 |

As is clear from the results shown in Table 3, the absorbability of insulin of the preparation (a) according to the present invention is extremely superior to that of the comparative preparation (b).

We claim:

1. An intranasally applicable powdery pharmaceutical composition comprising a pharmaceutically effective amount of a polypeptide having a physiological activity and about 0.001% to 12% by weight, based on the total weight of the composition, of at least one quaternary ammonium compound selected from the group consisting of benzalkonium chloride, benzethonium chloride, cetyl trimethyl ammonium bromide, and dodecyl dimethyl ammonium bromide in at least one lower alkyl ether of cellulose selected from the group consisting of hydroxypropyl cellulose, methyl cellulose, hydroxyethyl cellulose and hydroxpropylmethyl cellulose.

2. A powdery pharmaceutical composition as claimed in claim 1, wherein the polypeptide has a molecular weight of 300 to 300,000.

3. A powdery pharmaceutical composition as claimed in claim 1, wherein the polypeptide is at least one member selected from the group consisting of peptide hormones, physiologically active proteins, zymoproteins, and vaccines.

4. A powdery pharmaceutical composition as claimed in claim 3, wherein the peptide hormones include calcitonin, insulin luteinzing hormone-releasing hormones, desmopressin, vasopressin, oxytocin, and inteferons.

5. A powdery pharmaceutical composition as claimed in claim 1, wherein the quaternary ammonium compound is benzalkonium chloride or benzethonium chloride.

6. A powdery pharmaceutical composition as claimed in claim 1, wherein the lower alkyl ether of cellulse is hydroxypropyl cellulose.

7. A powdery pharmaceutical composition as claimed in claim 1, wherein the quaternary ammonium compound is included therein in an amount of about 0.025% to 1% by weight based on the total weight of the composition.

8. A powdery pharmaceutical composition of claim 1, wherein the composition is prepared by mixing (i) a lyophilized mixture of the polypeptide having a physiological activity, a portion or total amount of the quaternary ammonium compound, and a portion of the lower alkyl ether of cellulose, (ii) the remainder of the lower alkyl ether of cellulose, and, optionally (iii) the quaternary ammonium.

9. A powdery pharmaceutical composition as claimed in claim 8, wherein the amount of the component (ii) is 0.01% to 10% by weight of the total amount of the lower alkyl ether of cellulose in the composition.

10. A powdery pharmaceutical composition as claimed in claim 1, wherein at least about 90% by weight of the powder particles of the pharmaceutical composition has an effective particle diameter of about 10 to 250 μm.

11. A powdery pharmaceutical preparation in unit dosage form for application to the mucosa of the nasal cavity comprising the powdery pharmaceutical composition of claim 1.

12. A powdery pharmaceutical preparation as claimed in claim 11, wherein the pharmaceutical composition is included in a capsule.

* * * * *